United States Patent [19]

Phillips et al.

[11] Patent Number: 4,676,781
[45] Date of Patent: Jun. 30, 1987

[54] INJECTOR

[75] Inventors: Ian R. Phillips, Killara; Mervyn F. Reynolds, Balgowlah; Robert H. Lodge, Wheeler Heights, all of Australia

[73] Assignee: N.J. Phillips Pty. Limited, New South Wales, Australia

[21] Appl. No.: 799,192

[22] Filed: Nov. 18, 1985

Related U.S. Application Data

[63] Continuation of Ser. No. 563,029, Dec. 19, 1983, abandoned.

[30] Foreign Application Priority Data

Dec. 31, 1982 [AU] Australia ............... PF7464

[51] Int. Cl.$^4$ ............................................. A61M 5/20
[52] U.S. Cl. .................... 604/135; 604/136; 604/184
[58] Field of Search ............ 604/134, 135, 137, 700, 604/184, 186, 187, 136

[56] References Cited

U.S. PATENT DOCUMENTS 4,403,989 9/1983 Christensen ................... 604/137

FOREIGN PATENT DOCUMENTS 0074836 3/1983 European Pat. Off. .
0080112 6/1983 European Pat. Off. .
1491840 7/1971 Fed. Rep. of Germany ...... 604/136
847914 9/1960 United Kingdom .
1382941 2/1975 United Kingdom .
1449986 9/1976 United Kingdom .

OTHER PUBLICATIONS

PCT Application 81/00210

Primary Examiner—John D. Yasko
Attorney, Agent, or Firm—Ladas & Parry

[57] ABSTRACT

An injector to deliver a predetermined quantity of liquid into an animal, said injector having a hollow body with a handle, an interacting piston and cylinder mounted within the body and cooperating to define a variable volume working space, an injector needle communicating with said space, a passage also communicating with said space to enable the delivery of liquid thereto, a shroud to selectively cover said needle, and wherein movement of said shroud beyond a predetermined position exposing said needle enables relative movement between the piston and cylinder to eject liquid through said needle.

11 Claims, 4 Drawing Figures

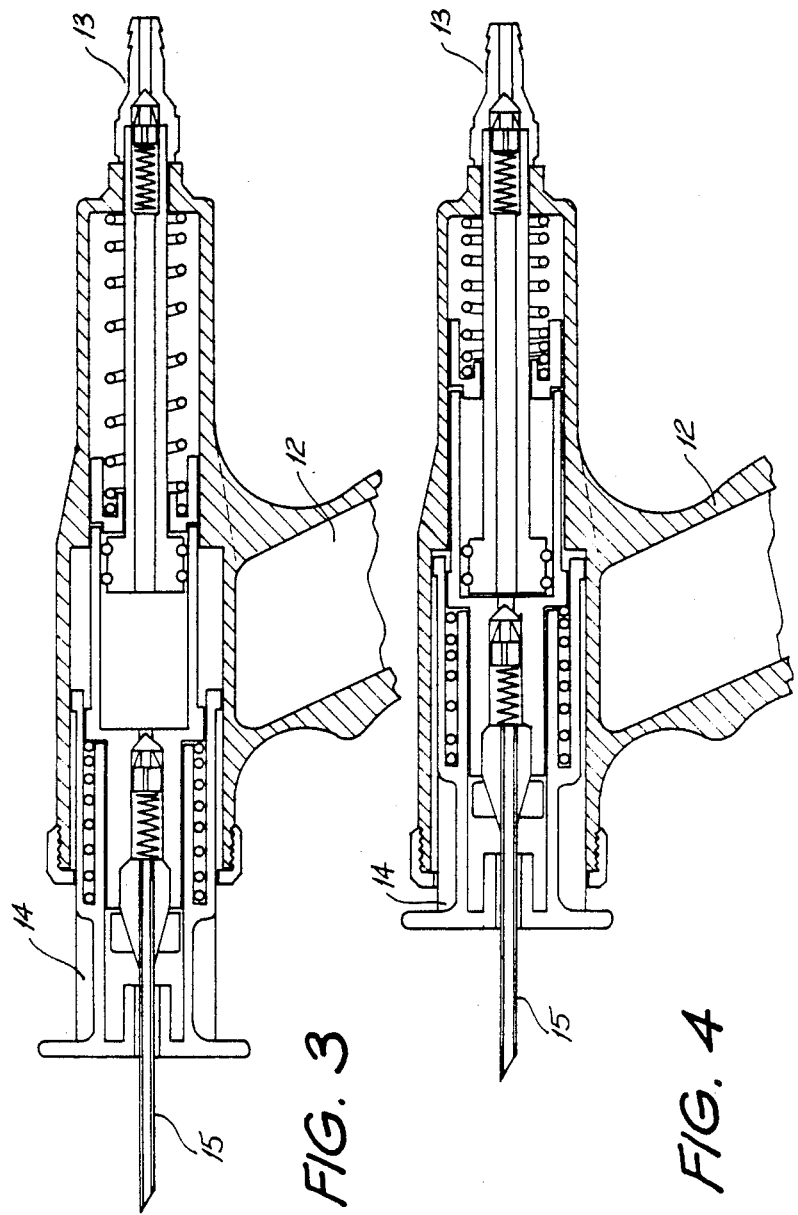

INJECTOR

This is a continuation of co-pending application Ser. No. 563,029 filed on Dec. 19, 1983, now abandoned.

The present invention relates to injectors and more particularly, but not exclusively, to injectors which deliver a predetermined dose of liquid into an animal.

Most injectors used require two actions to be performed by the user. One action is to insert the needle and the other action is to operate a trigger to force the desired dose through the needle and into the animal. This has the disadvantage that due to movement of the animal it is difficult to coordinate the two operations.

It is the object of the present invention to overcome or substantially ameliorate the above disadvantage.

There is disclosed herein an injector to deliver a predetermined quantity of liquid, said injector comprising a body having a handle to be gripped by the user, an interacting piston and cylinder mounted within the body and cooperating to define a variable volume working space, a piston rod extending from said piston and outwardly of said cylinder and fixed to said body, a first passage extending through said piston and piston rod so as to provide for the passage of liquid to said space, a second passage extending from said cylinder and adapted to receive an injecting needle so that liquid may be delivered from said space, a retractable shroud covering said needle, said shroud being movably mounted on said body so as to be retractable to a position exposing said needle, valve means to restrict movement of the liquid in a direction from said first passage to said second passage, and wherein movement of said shroud, to expose said needle, beyond a predetermined position causes movement of said cylinder to thereby reduce the volume of said space thus moving liquid under pressure through said second passage.

A preferred form of the present invention will now be described by way of example with reference to the accompanying drawings, wherein:

FIG. 3 is a schematic sectioned side elevation of the injector of FIG. 1 with a shroud exposing the needle of the injector; and FIG. 4 is a schematic sectioned side elevation of the injector of FIG. 1 with the shroud fully retracted.

Figure 1:
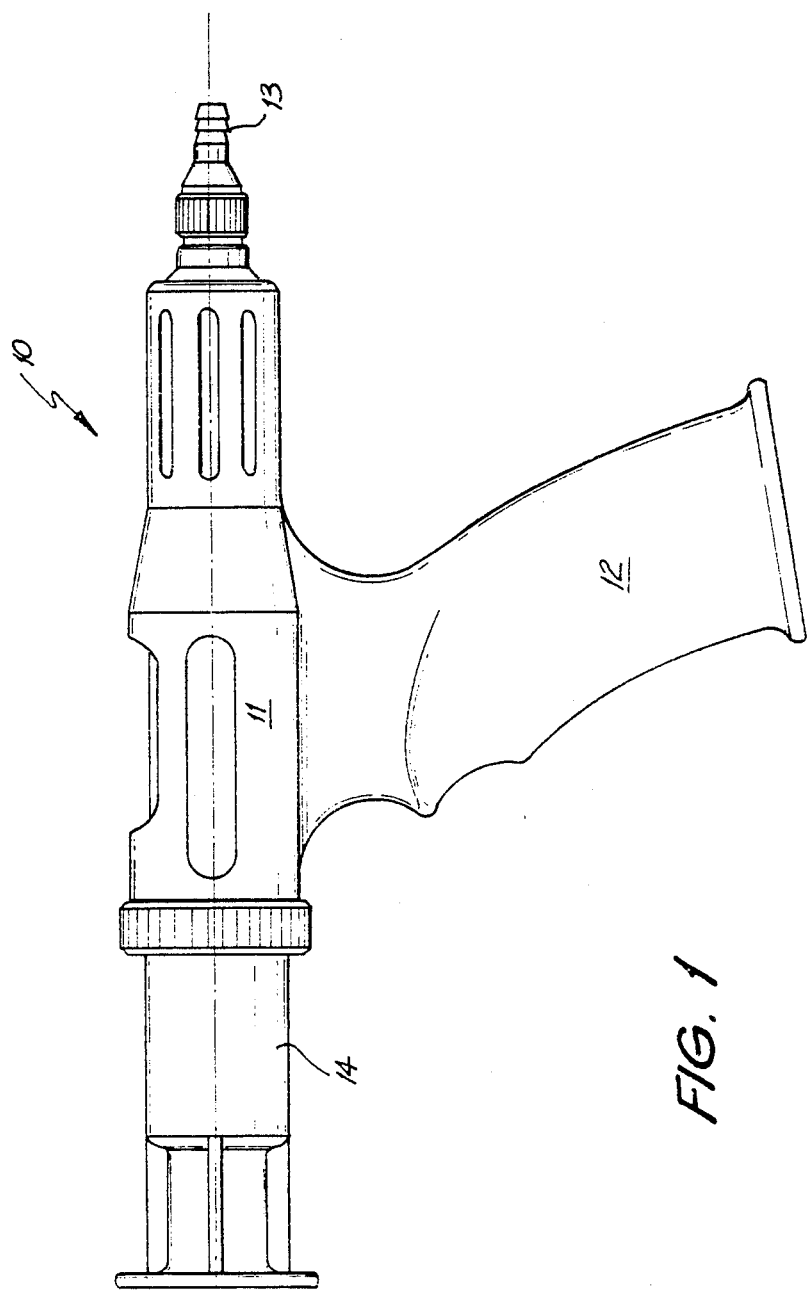
FIG. 1 is a schematic side elevation of an injector to deliver a liquid directly into the rumen of an animal.
Figure 2:
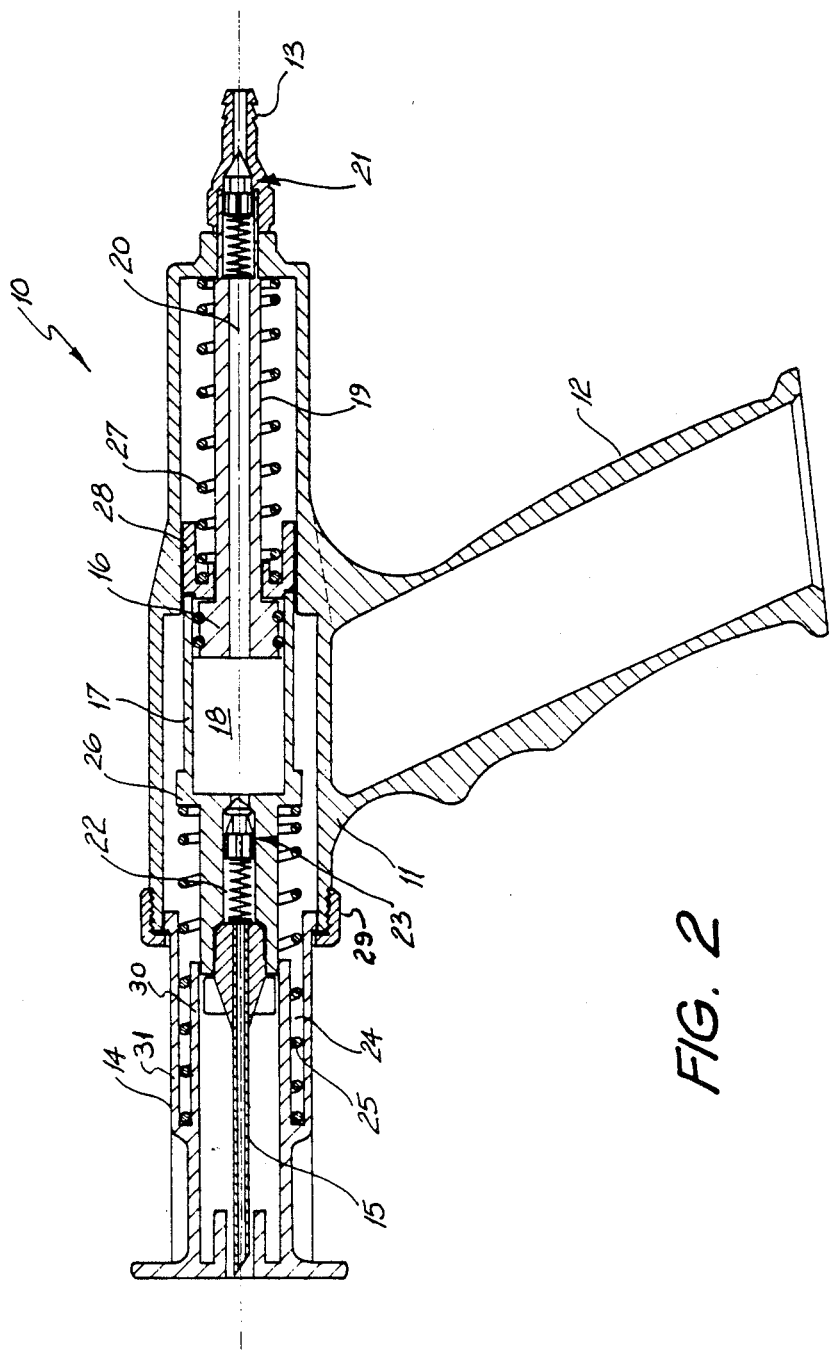
FIG. 2 is a schematic sectioned side elevation of the injector of FIG. 1.

In FIG. 1 there is schematically depicted an injector 10 having a hollow body 11 which provides a handle 12 to be gripped by a user. Extending from one end of the body 11 is a spigot connector 13 which is adapted to be attached to a flexible conduit which leads to a reservoir of liquid to be injected by the injector 10. The other end of the injector 10 is provided with a retractable shroud 14 which surrounds an injector needle 15. Mounted within the body 11 is an interacting piston 16 and cylinder 17 which cooperate to define a variable volume working space 18. Extending from the piston 16 is a piston rod 19, which is attached at one end to the body 11. The piston rod 19 is provided with a passage 20 which houses a one-way valve assembly 21 through which liquid passes from the spigot connector 13.

The cylinder 17 is provided with a passage 22 which communicates with the needle 15 so that liquid may pass from the space 18 to be delivered by the needle 15. Mounted within the passage 22 is a one-way valve assembly 23 which, in combination with the one-way valve assembly 21, restricts the liquid to pass through the device 10 in one direction, that is from the connector 13 to the needle 15.

The shroud 14 is slidably mounted within the body 11 and is provided with an annular recess 24 which receives a portion of the spring 25 which also abuts a flange 26 on the cylinder 17. The spring 25 biases the shroud 14 to its extended outward position. Surrounding the piston rod 19 is a spring 27 which engages a slide member 28 which abuts the cylinder 17. The slide member 28 also abuts the piston when the piston 16 and cylinder are in a position defining maximum volume for the space 18. The shroud is attached to the body 11 by a retaining ring.

The annular recess 24 provides two annular sleeves 30 and 31, with the sleeve 30 engaging the cylinder 17 to cause movement thereof upon the shroud 14 moving beyond a predetermined position. The sleeve 31 defines the stop position of the shroud 14 and cylinder 17 by abutment with the body. The shroud 14 also has a guide passage for slidable engagement with the needle 15.

As can be seen from FIGS. 3 and 4, in operation of the injector 10 the shroud 14 is placed in the relevant location on the hide of the animal and the user pushes against the animal in a continuous motion to cause the needle to penetrate the rumen and to deliver the dose. The first stage of operation includes the retraction of the shroud 14 and the exposing of the needle 15, whereupon subsequent movement of the shroud 14 beyond a predetermined position causes movement of the cylinder 17, by engagement of the shroud 14 therewith, and the subsequent decreasing of the volume of the space 18 to thereby force liquid through the needle 15. The sequence of operation is achieved by the spring 27 having a greater spring rate than the spring 25.

What we claim is:

1. An injector to deliver a predetermined quantity of liquid into an animal, said injector comprising a body having a handle to be gripped by the user, an interacting piston and cylinder mounted within the body and movable relative to each other so as to cooperate in defining a variable volume working space of cylindrical configuration, spring means biasing said piston and cylinder to move relative to each other to maximize the volume of said space, one said piston and said cylinder being fixed to said body, and other being movable relative thereto, a first passage extending from said space enabling liquid to be delivered to said space via said first passage, a second passage extending from said space and adapted to receive an injection needle so that liquid may be delivered from said space through said second passage, a retractable shroud covering said needle, said shroud being movably mounted on said body so as to be retractable to a predetermined position exposing said needle by an operator gripping said handle and applying a force thereto to move said handle towards said animal, valve means to restrict movement of the liquid in a direction from said first passage to said second passage, and wherein when said shroud moves beyond said predetermined position said shroud engages one said piston and cylinder to cause relative movement therebetween by said operator pushing one said piston and cylinder, relative to the other by continuing to apply a force to said handle, thereby reducing the volume of said space to move liquid under pressure through said second passage.

2. The injector of claim 1 further including a first spring biasing said shroud to an extended position to cover said needle.

3. The injector of claim 1 further comprising a piston rod extending from said piston and outwardly of said cylinder to a position fixing to said body, said spring means includes a second spring biasing said cylinder to move relative to said piston to a position wherein said space has a maximum volume so as to draw liquid into said space via said first passage, and said first passage extends through said piston and piston rod and said second passage extending from said cylinder.

4. The injector of claim 1 or 2 further including a piston rod affixed to said piston and extending outwardly of said cylinder with said piston affixed to said body, and wherein said first passage extends through said piston and piston rod and said second passage extends from said cylinder, and upon shroud reaching said predetermined position, said shroud abuts said cylinder to move same.

5. The injector of claim 2, wherein said shroud has an annular recess within which said first spring is located upon retraction of said shroud to expose said needle.

6. The injector of claim 5, wherein the extremity of said shroud has a guide to slidably engage said needle.

7. The injector of claim 3, further including a slidable member located on said piston rod so as to be movable longitudinally thereof, and wherein said cylinder abuts said slidable member and said second spring bears against said slidable member to bias said cylinder to a position maximising the volume of said space.

8. The injector of claim 2, wherein said first spring bears against said shroud and cylinder.

9. The injector of claim 3, wherein said second spring has a greater spring rate than said first spring.

10. The injector according to claim 1 wherein said operator pushes said cylinder which is movable relative said piston.

11. The injector according to claim 1 wherein said operator pushes said piston which is movable relative said cylinder.

* * * * *